United States Patent
Davis et al.

(10) Patent No.: US 9,050,447 B2
(45) Date of Patent: Jun. 9, 2015

(54) POSITIVE BOLUS CLAMP

(75) Inventors: Denton Davis, San Diego, CA (US); Jonathan Walborn, Mission Viejo, CA (US); Roger Greenwald, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 375 days.

(21) Appl. No.: 13/304,222

(22) Filed: Nov. 23, 2011

(65) Prior Publication Data

US 2013/0131608 A1     May 23, 2013

(51) Int. Cl.
*F16K 7/04* (2006.01)
*A61M 39/28* (2006.01)
*F16L 55/10* (2006.01)

(52) U.S. Cl.
CPC ............. *A61M 39/28* (2013.01); *F16L 55/10* (2013.01); *A61M 39/287* (2013.01); *F16K 7/04* (2013.01)

(58) Field of Classification Search
CPC ..... A61M 39/287; A61M 39/28; F16L 55/10; F16K 7/04
USPC ............. 251/4, 6, 9, 10; 604/33, 249, 250, 34
See application file for complete search history.

(56) References Cited

U.S. PATENT DOCUMENTS

| | | | | |
|---|---|---|---|---|
| 2,092,400 | A | * | 9/1937 | Miller ................. 251/7 |
| 2,775,240 | A | * | 12/1956 | Morrisey, Jr. et al. ........ 604/405 |
| 3,374,509 | A | * | 3/1968 | Logan et al. .................... 24/570 |
| 4,248,401 | A | * | 2/1981 | Mittleman ......... 251/7 |
| 4,307,869 | A | * | 12/1981 | Mittleman ......... 251/7 |
| D279,314 | S | * | 6/1985 | Ishida et al. ................. D24/143 |
| 4,932,629 | A | * | 6/1990 | Rodomista et al. .............. 251/4 |
| 5,453,098 | A | * | 9/1995 | Botts et al. ..................... 604/249 |
| 5,817,083 | A | * | 10/1998 | Shemesh et al. ............. 604/416 |
| 5,853,398 | A | * | 12/1998 | Lal et al. ......................... 604/250 |
| 6,117,115 | A | * | 9/2000 | Hill et al. ....................... 604/250 |
| 6,840,492 | B1 | * | 1/2005 | Boyne-Aitken .................. 251/7 |
| D638,932 | S | * | 5/2011 | She et al. ..................... D24/129 |
| 2001/0039403 | A1 | * | 11/2001 | Lynn ............................. 604/250 |
| 2006/0224128 | A1 | * | 10/2006 | Lurvey et al. ................. 604/250 |

* cited by examiner

*Primary Examiner* — Craig Schneider
*Assistant Examiner* — Frederick D Soski
(74) *Attorney, Agent, or Firm* — McDermott Will & Emery LLP

(57) ABSTRACT

A clamp for clamping flexible tubing is disclosed. The clamp includes a body having a first portion, a second portion, a first passage through the first portion, and a second passage through the second portion. The first passage is configured to compress a first length of the flexible tubing when the flexible tubing is displaced laterally into the first passage. The second passage is configured to compress a second length of the flexible tubing that does not overlap the first length when the flexible tubing is displaced laterally into the second passage.

5 Claims, 6 Drawing Sheets

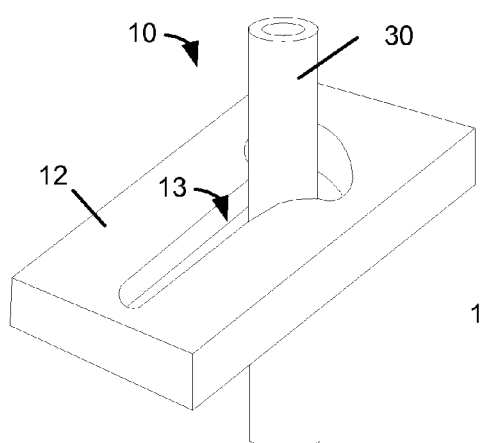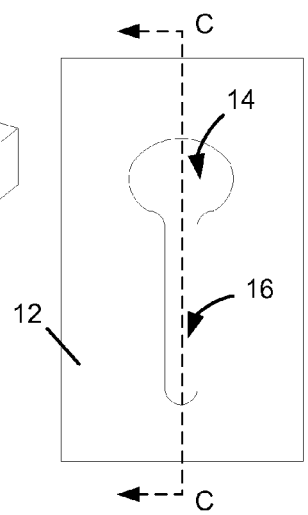
FIG. 1A  
(PRIOR ART)
FIG. 1B  
(PRIOR ART)
FIG. 1C  
(PRIOR ART)
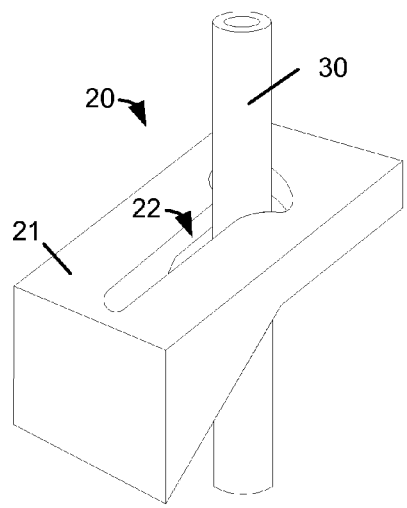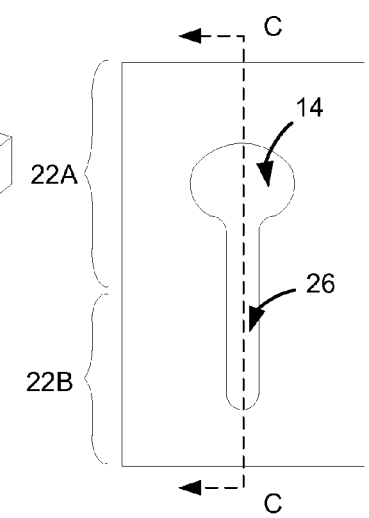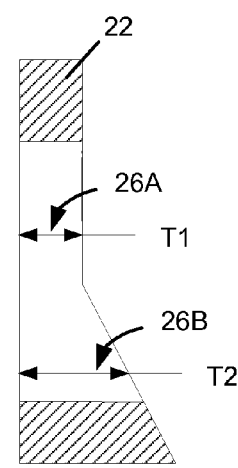
FIG. 2A
FIG. 2B
FIG. 2C

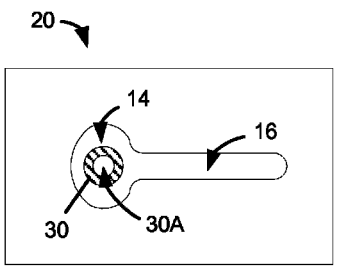
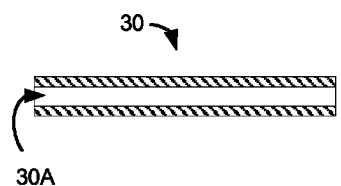
FIG. 3A  FIG. 3B
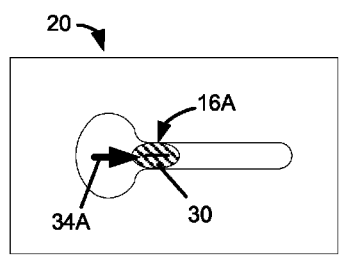
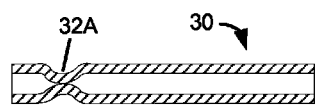
FIG. 4A  FIG. 4B
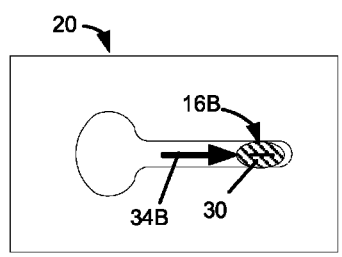
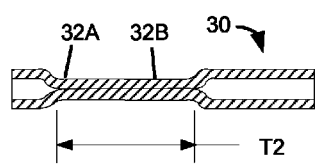
FIG. 5A  FIG. 5B

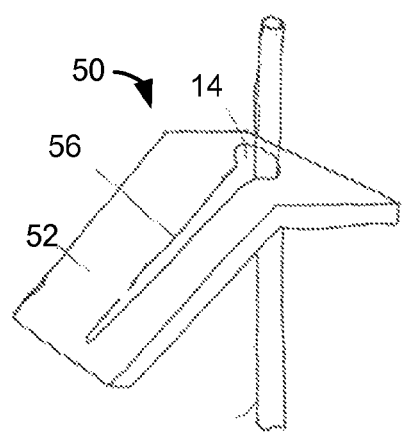
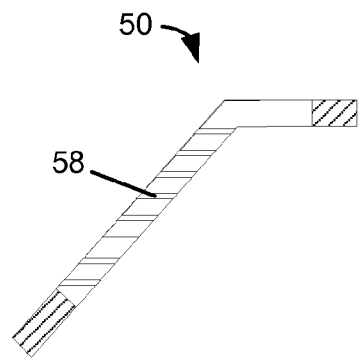
FIG. 9A　　　　　　　　　　FIG. 9B
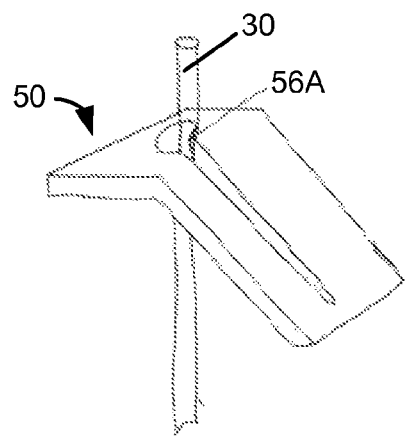
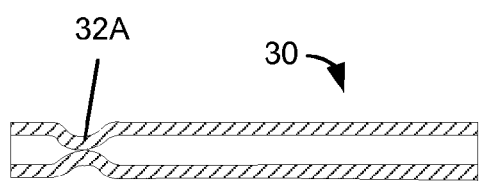
FIG. 10A　　　　　　　　　　FIG. 10B
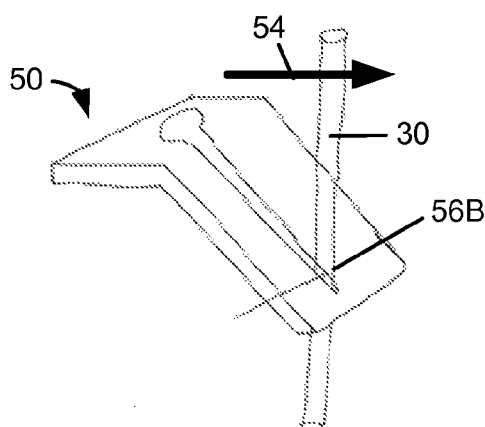
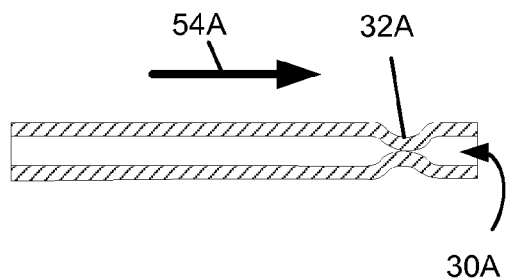
FIG. 11A　　　　　　　　　　FIG. 11B

POSITIVE BOLUS CLAMP

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

1. Field

The present disclosure generally relates to intravenous (IV) administration of medical fluids and, in particular, tubing clamps for use with the tubing of IV sets.

2. Description of the Related Art

Medical procedures often require the IV administration of various fluids such as medications via a programmable pump, gravity-fed IV bag, or injection. For example, liquid saline solution is commonly administered intravenously to patients who cannot take fluids orally and have developed severe dehydration. Typically, the IV fluid administration takes place at periodic intervals over a length of time and patient treatment requires additional delivery of other therapeutic fluids. A catheter is often inserted into the patient's vein, the proximal end of which is connected to medical tubing. The medical tubing in turn is connected to a source of medical fluid, such as an IV bag. In order to avoid repeated direct injections into the patient, sections of the medical tubing between the catheter and the primary fluid source often include "Y" branches, which include connectors. These connectors allow the attachment of syringe devices or other sources of medical fluid to deliver additional medical fluids to the patient via the already implanted catheter. The combination of medical tubing, fitting, and connectors is commonly referred to as an "IV set."

A positive bolus effect describes the condition in which fluid is flushed out of the connector during removal of the syringe from the connector. A zero bolus effect describes the condition during which no fluid displacement takes place, and fluid is neither drawn into nor flushed out of the connector during removal of the syringe.

A problem associated with typical IV sets is the creation of a negative bolus effect upon withdrawal of a syringe from a "Y" connector. A negative bolus effect is generated when a partial vacuum is produced within the connector upon removal of the syringe. This partial vacuum may draw fluid up from the medical line tubing and into the connector. The tubing draws fluid from the catheter connected to the patient, which in turn draws fluid, such as blood, from the patient. This drawing of fluid from the patient into the IV set may contaminate the IV set or blood that is drawn into the IV set may clot and form an obstruction to future fluid flow through the IV set.

One method of reducing the negative bolus effect is to provide a clamp over the tubing to be used in conjunction with mating or removing a syringe or other source of medical fluid. The clamp is attached to a portion of the medical line tubing that is downstream from the connector and pinches the tubing closed. The negative bolus effect is therefore limited to the section of tubing between the Y-connector and the clamp. There may be a partial vacuum created in the line, however, and this partial vacuum will also cause a retrograde flow of blood or other fluid from the patient if the clamp is released.

The negative bolus effect may be also be overcome by use of a positive bolus connector. Such a connector, typically a female needleless connector, has a variable volume internal flow path that expands when a male connector is mated to it. When the male connector is removed, the internal flow path contracts and expels fluid into the line, thereby creating a positive bolus. A user accustomed to standard connectors may actuate a standard tubing clamp just downstream of the connector, as described above, before disconnecting the positive bolus connector, thereby defeating the positive bolus feature of the connector.

SUMMARY

There is a need for a simple-to-use positive bolus clamp that can be used with all types of connectors effectively create a positive bolus of fluid.

The above and other needs are met by the disclosed embodiments, which provide a clamp apparatus for advantageously preventing fluid flow through resilient flexible tubing at an upstream location and collapsing a down-stream portion of the tubing to provide a positive bolus of fluid out of the tubing towards the patient.

In certain embodiments, a clamp for clamping flexible tubing is disclosed. The clamp includes a body having a first portion, a second portion, a first passage through the first portion, and a second passage through the second portion. The first passage is configured to compress a first length of the flexible tubing when the flexible tubing is displaced laterally into the first passage. The second passage is configured to compress a second length of the flexible tubing that does not overlap the first length when the flexible tubing is displaced laterally into the second passage.

In certain embodiments, a clamp for clamping flexible tubing is disclosed that includes a first element having a first surface with a first corner, a second element having a second surface with a second corner; and a flexible element coupled to the first and second elements. The flexible element is configured such that when the clamp is not actuated, the first and second surfaces are disposed at an angle to each other. The flexible element is further configured such that when the first element is displaced toward the second element with the flexible tubing between the first and second elements, the first and second corners cooperate to sealingly compress a first length of the flexible tubing. As the first element is further displaced toward the second element, the first element rotates with respect to the second element such that the first and second surfaces cooperate to sealingly compress a second length of the flexible tubing.

In certain embodiments, a method of clamping flexible tubing is disclosed. The method includes the steps of laterally displacing the flexible tubing into a first passage configured to sealingly compress a first length of the flexible tubing and further displacing laterally the flexible tubing into a second passage configured to sealingly compress a second length of the flexible tubing that does not overlap the first length.

In certain embodiments, a method of clamping flexible tubing is disclosed. The method includes the steps of displacing a first element having a first surface with a first corner toward a second element having a second surface with a second corner with the flexible tubing disposed between the first and second surfaces until the first and second corners cooperate to sealingly compress the flexible tubing and further displacing the first element toward the second element thereby causing the first element to rotate relative to the second element such that the first and second surfaces cooperate to sealingly compress a second length of the flexible tubing.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 1A, 1B, and 1C are perspective, front, and lateral cross-sectional views of a prior art slide clamp.

FIGS. 2A, 2B, and 2C are perspective, front, and lateral cross-sectional views of an exemplary embodiment of a positive bolus clamp according to certain aspects of the disclosure.

FIGS. 3A, 3B, 4A, 4B, 5A, and 5B depict operational configurations of the clamp of FIGS. 2A-2C according to certain aspects of the disclosure.

FIGS. 9A and 9B are perspective and lateral cross-sectional views of another embodiment of a positive bolus clamp according to certain aspects of the disclosure.

FIGS. 10A, 10B, 11A, and 11B depict operational configurations of the clamp of FIGS. 9A-9B according to certain aspects of the disclosure.

DETAILED DESCRIPTION

Figures 6A, 6B, 6C:
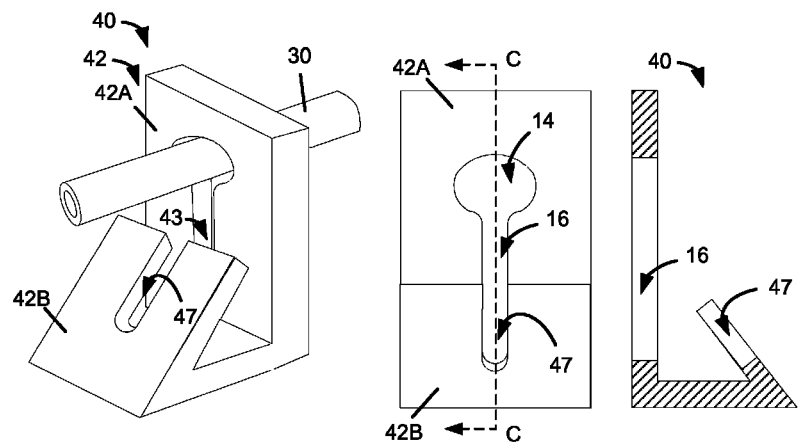
FIGS. 6A, 6B, and 6C are perspective, front, and lateral cross-sectional views of another embodiment of a positive bolus clamp according to certain aspects of the disclosure.

The embodiments and methods disclosed herein are presented in terms of exemplary clamps being used with flexible tubing that is part of an IV set configured to delivery medical fluids to a patient in a healthcare setting. It will be obvious to those of ordinary skill in the art, however, that this same configuration and method can be utilized in a variety of applications where it is desirable to restrict or stop the flow of liquid through flexible tubing and force a bolus of the fluid in a particular direction as the flow is stopped. Nothing in this disclosure should be interpreted, unless specifically stated as such, to limit the application of any method or system disclosed herein to a medical application or use with IV set.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Within this disclosure, reference is made to directions relative to the medical tubing 30 with which the various example embodiments of a positive bolus clamp are being used. The phrase "along the tube" refers to a direction aligned with the long direction of the tubing 30. The phrases "lateral" or "laterally" refer to a direction that is perpendicular to the length of the tubing 30. The phrase "displaced laterally" refers to movement of the tubing 30 in a lateral direction, i.e. the tube is moving perpendicular to the long direction of the tubing 30. The phrase "contiguous" as used with respect to slots and passages of a clamp indicates that the open spaces of the two referenced elements are open to each other such that an object, such as tubing 30, that is passing through one of the referenced elements may pass into the other referenced element without being disengaged from the clamp.

FIGS. 1A, 1B, and 1C are perspective, front, and lateral cross-sectional views of a prior art slide clamp 10. The clamp 10 comprises a base 12 with a slot 13 penetrating the base 12 and flexible tubing 30 passing through the slot 13.

FIG. 1B illustrates that the slot 13 comprises non-obstructing passage 14 and a first passage 16 arranged on the slide clamp 10. The non-obstructing passage 14 and first passage 16 are configured relative to one another such that conventional diameter medical tubing 30 would not be occluded in the non-obstructing passage 14 but would be occluded in first passage 16. The width of the slot of the first passage 16 is sufficiently small that a selected tube 30 passing through the first passage 16 would be completely occluded and would remain occluded against a foreseeable range of fluid pressures in the tubing 30. The range of pressures against which the tubing 30 would remain occluded would include at least the static head anticipated during normal use of standard infusion apparatus.

FIG. 1C depicts a cross-section of body 12 along the section line C-C of FIG. 1B. It can be seen that the clamp 10 will surround the tubing 30 once clamp 10 is placed over the tubing 30 such that the clamp 10 will not be lost or dropped.

FIGS. 2A, 2B, and 2C are perspective, front, and lateral cross-sectional views of an exemplary embodiment of a positive bolus clamp 20 according to certain aspects of the disclosure. The positive bolus clamp 20, which can be considered to be a ramp shut-off slide clamp 20, comprises a body 22 with a slot 23 with tubing 30 passing through the slot 23 such that the slot 23 is generally perpendicular to the direction of the sliding movement of the slide clamp 20 relative to the tubing 30.

FIG. 2B shows that the body 22 has a first portion 22A and a ramped second portion 22B. The ramp shut off slide clamp 20 is penetrated from its top surface 21 by an elongated aperture 22. The aperture 22 comprises a non-obstructing passage 14 and an occluding passage 26 that is divided into a first passage 26A and a second passage 26B. The non-obstructing passage 14 is sized such that a conventional medical line tube 30 would not be occluded. When the clamp 20 is moved across the medical tubing 30, the occluding portion 26 is sized such that it occludes the medical tubing 30. The width of the occluding portion 26 is sized so that the selected medical line tubing 30 passing through the occluding portion 26 would be completely occluded and would remain occluded against a foreseeable range of fluid pressures in the medical line tube 30. The first portion 22A is penetrated by the first passage 26A. The second portion 22B is penetrated along its angled surface by the second passage 26B. The widths of the first passage 26A and the second passage 26B are both sized so that a medical tube 30 would be completely occluded and remain occluded against a foreseeable range of fluid pressures in the medical tube 30.

FIG. 2C is the cross-section taken at section line C-C in FIG. 2B. FIG. 2C illustrates that, in certain embodiments, the first passage 26A has substantially uniform thickness T1 whereas the second passage 26B has a variable thickness T2. In certain embodiments, the thickness T2 varies as the distance from the point of measurement to the boundary between portions 22A and 22B increases. In certain embodiments, the thickness T2 is proportional to the distance from the boundary between portions 22A and 22B. It can also be seen in FIG. 2C that the medical tubing 30 is captured by the body 22 such that the clamp 20 will not be lost or dropped. In certain embodiments, the body 22 comprises a split line (not shown) such that the medical tubing 30 may be laterally introduced into the slot 23. In certain embodiments, this split line has a locking feature (not shown) such that the split line may be locked once a medical tubing is located in slot 23.

FIGS. 3A, 3B, 4A, 4B, 5A, and 5B depict operational configurations of the clamp 20 of FIGS. 2A-2C according to certain aspects of the disclosure. FIG. 3A depicts a front view of a clamp 20 with medical tubing 30 passing through the non-obstructing passage 14. FIG. 3B depicts a cross-sectional view of the medical tubing 30 with a flow channel 30A in the configuration of FIG. 3A. It can be seen in FIG. 3B that the flow channel 30A is fully open. The remaining pairs of FIGS. 4A/4B and 5A/5B also show matching views of their respective common configurations.

FIG. 4A depicts a configuration reached after the medical tubing 30 is laterally displaced into the first passage 26A to a position 16A within the slot 26 as indicated by arrow 34A. The flow channel 30A is sealingly compressed and is visible in FIG. 4A only as a line in the middle of the tube 30. FIG. 4B depicts the cross-sectional view of the configuration of FIG. 4A and shows that the tubing 30 is sealingly compressed over a length 32A sufficient to occlude the flow channel 30A.

FIG. 5A depicts a configuration reached after the medical tubing 30 is further laterally displaced from the first passage 26A into the second passage 26B to a position 16B within the slot 26. With reference back to FIG. 2C, the width T2 of this position 16B is greater than the width T1 of position 16A. This results in a second length 32B being sealingly compressed. As the length 32B was incrementally compressed starting from the configuration of FIG. 4A and extending to the right, in the view of FIG. 5B, as the tubing 30 was displaced to the right along passage 26 as indicated by arrow 34B, fluid in the flow channel 30A was forced to flow to the right, thus producing the positive bolus upon actuation of clamp 20.

FIGS. 6A, 6B, and 6C are perspective, front, and lateral cross-sectional views of another embodiment of a positive bolus clamp 40 according to certain aspects of the disclosure. The body 42 has a first portion 42A with a slot 43, similar to the body 12 and slot 13 of clamp 10. The body 42 also has a second portion 42B that is displaced from the first portion 42A in a direction along the flexible tubing 30. The first and second portions 42A, 42B are, in this embodiment, fixedly coupled together. In the embodiment of FIG. 6A, the second portion 42B comprises a U-shaped notch 47. In certain embodiments, other shapes combine tapered profiles with slots similar to first passage 16 are provided. In certain embodiments, the notch 47 is functionally equivalent to the second passage 26B of FIG. 2A as will be discussed in greater detail with respect to FIGS. 7A/7B and 8A/8B.

FIG. 6B illustrates that the notch 47 is aligned with the slot 43 in the left-right lateral direction, in the view of FIG. 6B. The slot 43 comprises a non-obstructing passage 14 that is contiguous with the first passage 16. In the view of FIG. 6B, the notch 47 is vertically positioned in alignment with a lower portion of first passage 16.

FIG. 6C is the cross-section taken at section line C-C in FIG. 6B. FIG. 6C illustrates that, in this embodiment, the second portion 42B is positioned away from the first portion 42A and also angled with respect to first portion 42A. It can be seen that the notch 47 is approximately horizontally aligned with the bottom portion of first passage 16 and that tubing passing horizontally, in the view of FIG. 6C, through the clamp 40 can simultaneously pass through the lower portion of first passage 16 and notch 47.

Figures 7A, 7B:
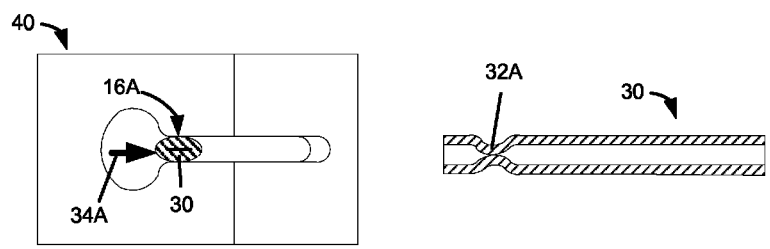
FIGS. 7A, 7B, 8A, and 8B depict operational configurations of the clamp of FIGS. 6A-6C according to certain aspects of the disclosure.

FIGS. 7A, 7B, 8A, and 8B depict operational configurations of the clamp 40 of FIGS. 6A-6C according to certain aspects of the disclosure. FIG. 7A depicts a configuration of the clamp 40 wherein medical tubing that was previously passing through the non-obstructing passage 14 has been laterally displaced as indicated by arrow 34A into the first passage 16 to a position 16A. The medical tubing 30 has been sealingly compressed and it can be seen that the flow channel 30A is fully obstructed as indicated by the line in the middle of tubing 30 being the only visible portion of the flow passage 30A.

FIG. 7B depicts the cross-sectional view of tubing 30 in the configuration of FIG. 7A. The tubing 30 is compressed over a first length 32A by the first passage 16.

Figures 8A, 8B:
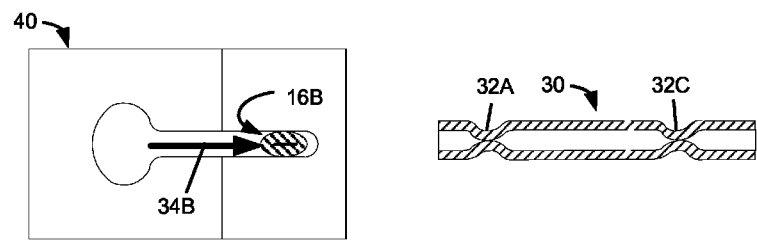

FIG. 8A depicts the configuration of clamp 40 and tubing 30 after the tubing 30 has been further laterally displaced as indicted by arrow 34B to a second position 16B in first passage 16. As the tubing 30 is displaced to position 16B, a portion of tubing 30 engages the angled notch 47 thereby sealingly compressing the tubing 30 over a second length 32C. The first passage 16 continues to sealingly compress tubing 30 over length 32A as the tubing is displaced from point 16A to point 16B. As the tubing 30 continues to be laterally displaced, the length 32C moves along the tubing 30 thereby forcing fluid out of tubing 30 to the right, in the view of FIG. 8B. It can be seen that in the configuration shown in FIGS. 8A and 8B, the tubing 30 is sealingly compressed by both the first passage 16 over first length 32A and the notch 47, functioning as a second passage, over the second length 32C.

FIGS. 9A and 9B are perspective and lateral cross-sectional views of another embodiment of a positive bolus clamp 50 according to certain aspects of the disclosure. The clamp 50 is configured as an angled shut-off slide having a body 52 with a slot 56 contiguous with a non-obstructing passage 14. The elongated dimension of the slot 56 is arranged on the angled portion of the body 52 to be aligned with the direction of sliding motion of the slide clamp 50 relative to the tubing 30 when actuating the clamp 50.

FIG. 9B is a cross-sectional view taken through the slot 56 of FIG. 9A. In this embodiment, the slot 56 comprises ridges 58 that are aligned with the intended direction of displacement of tubing 30 as it is laterally displaced from the non-obstructing passage 14 into slot 56. These ridges 58 assist the tubing 30 in moving horizontally, in the view of FIG. 9B, rather than sliding along the angled portion of body 52.

FIGS. 10A, 10B, 11A, and 11B depict operational configurations of the clamp 50 of FIGS. 9A-9B according to certain aspects of the disclosure. FIG. 10A illustrates the configuration of clamp 50 as the tubing 30 initially engages slot 56 at point 56A. FIG. 10B shows a cross-section of the tubing 30 while engaged by clamp 50 in the configuration of FIG. 10A. It can be seen that the tubing 30 has been sealingly compressed by the slot 56 over a length 32A.

FIG. 11A depicts a configuration of clamp 50 with respect to tubing 30 after the tubing 30 has been laterally displaced from the configuration of FIG. 10A in the direction indicated by the arrow 54 to a position 56B. It can be seen that the displacement is not aligned with the angled portion of body 52. FIG. 11B depicts the configuration of tubing 30 while in the configuration of FIG. 11A, showing that the length 32A has moved along the length of tubing 30 as indicated by arrow 54A as the tubing 30 was laterally displaced as indicated by arrow 54 in FIG. 11A. This displacement of length 32A along the tubing 30 causes the fluid that is in the flow channel 30A to flow to the right, in the view of FIG. 11B, thereby creating the positive bolus of fluid as fluid is gradually forced out of the tubing 30.

Figure 12:
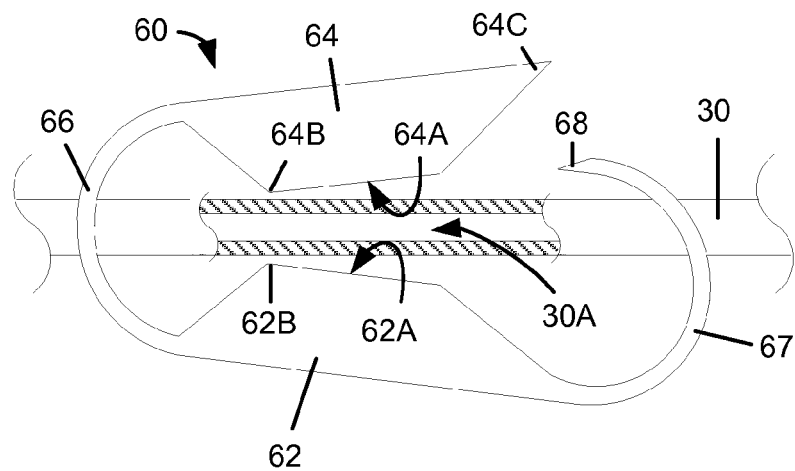
FIG. 12 depicts a lateral view of another embodiment of a positive bolus clamp according to certain aspects of the disclosure.

FIG. 12 depicts a lateral view of another embodiment of a positive bolus clamp 60 according to certain aspects of the disclosure. The C-clip clamp 60 comprises a first element 62 having a first surface 62A with a first corner 62B and a second element 64 having a second surface 64A with a second corner 64B. The first and second elements 62, 64 are coupled together by a flexible element 66. The clamp 60 also includes a latching arm 67 with a latching tip 68 that is configured to retain the tip 64C of the first element 64. The flexible element 66 and the latching arm 67 are penetrated by holes (not visible in FIG. 12) that are coincident with the locations where the tubing 30 is seen to pass through the respective flexible element 66 and latching arm 67, wherein the tubing 30 passes through these holes. In certain embodiments, the holes through the flexible element 66 and latching arm 67 are open to the far side of the clamp 60, in the view of FIG. 12, such that the clamp 60 can be placed over tubing 30 without having to disconnect the tubing 30 from either end. It can be seen that the surfaces 62A and 64A are disposed at an angle to each other and that there is sufficient space between the corners 62B and 64B that the tubing 30, shown in partial cross-section in FIGS. 12-14, is not compressed and the flow channel 30A is not fully occluded when the clamp 60 is not actuated as depicted in FIG. 12.

Figure 13:
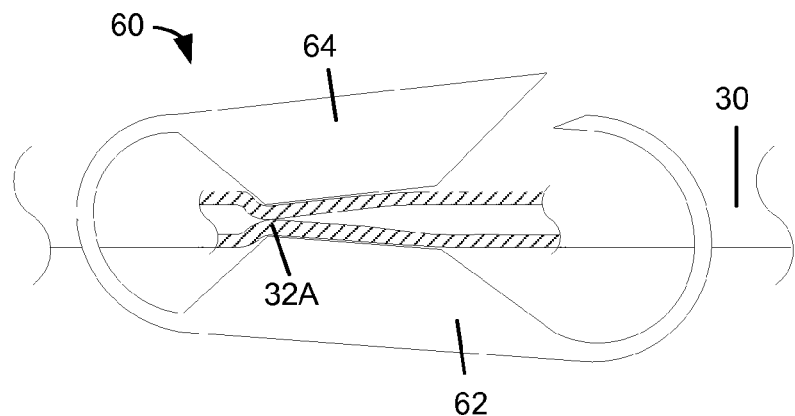
FIGS. 13 and 14 depict operational configurations of the clamp of FIG. 12 according to certain aspects of the disclosure.
Figure 14:
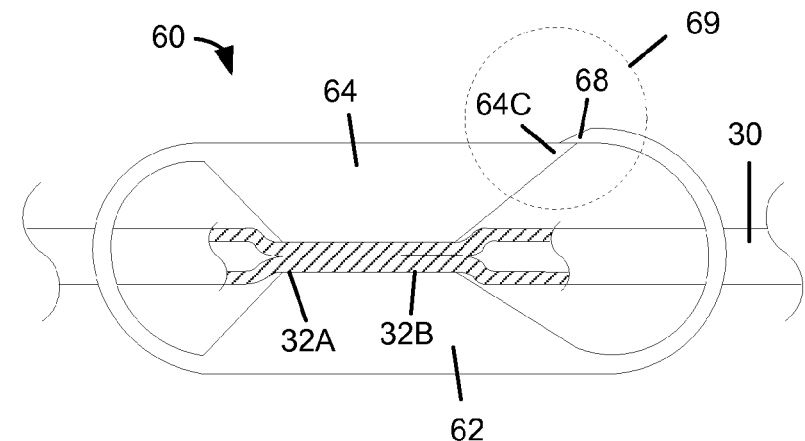

FIGS. 13 and 14 depict operational configurations of the clamp of FIG. 12 according to certain aspects of the disclosure. FIG. 13 depicts the configuration of clamp 60 and tubing 30 after the clamp 60 has been partially actuated. The first element 62 has been displaced toward the second element 64 with the tubing 30 disposed between the first and second elements 62, 64. In this configuration, the first and second corners 62B, 64B have closed the gap of FIG. 12 thereby cooperatively compressing the first length 32A of the tubing 30 so as to occlude the flow channel 30A.

FIG. 14 depicts the configuration of clamp 60 and tubing 30 after the clamp 60 is fully actuated. To reach the configuration of FIG. 14 from the configuration of FIG. 13, the first element 62 is further displaced toward the second element 64. The first element 62 rotates with respect to the second element 64 such that the first and second surfaces 62A, 64A cooperate to sealingly compress a second length 32B of the tubing 30. It can be seen that the first length 32A remains compressed while the second length 32B is compressed by the further actuation of the clamp 60. The latching tip 68 and the tip 64C together form a retention feature 69 that retains the clamp 60 in the configuration of FIG. 14 until released by a user by displacing the latching tip 68 away from the tip 64C.

Figure 15:
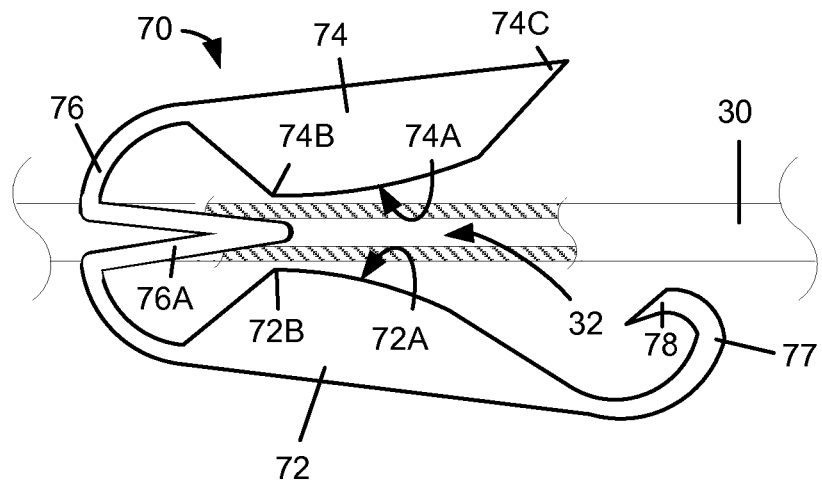
FIG. 15 depicts a lateral view of another embodiment of a positive bolus clamp according to certain aspects of the disclosure.

FIG. 15 depicts a lateral view of another embodiment of a positive bolus clamp 70 according to certain aspects of the disclosure. The C-clip clamp 70 comprises a first element 72 having a first surface 72A with a first corner 72B and a second element 74 having a second surface 74A with a second corner 74B. It can be seen that the first and second surfaces 72A, 72B are curved. The first and second elements 72, 74 are coupled together by a flexible element 76 that comprises a folded element 76A. The clamp 70 also includes a latching arm 77 with a latching tip 78 that is configured to retain the tip 74C of the first element 74. The flexible element 76 and the latching arm 77 are penetrated by holes (not visible in FIG. 15) that are coincident with the locations where the tubing 30 is seen to pass through the respective flexible element 76 and latching arm 77, wherein the tubing 30 passes through these holes. In certain embodiments, the holes through the flexible element 76 and latching arm 77 are open to the far side of the clamp 70, in the view of FIG. 15, such that the clamp 70 can be placed over tubing 30 without having to disconnect the tubing 30 from either end. It can be seen that the surfaces 72A and 74A are disposed at an angle to each other, comparing reference planes (not shown) of surfaces 72A, 74A passing between the two respective corners of each surface 72A, 74A. It can be seen that that there is sufficient space between the corners 72B and 74B that the tubing 30, shown in partial cross-section in FIGS. 15-17, is not compressed and the flow channel 30A is not occluded when the clamp 70 is not actuated as depicted in FIG. 15.

Figure 16:
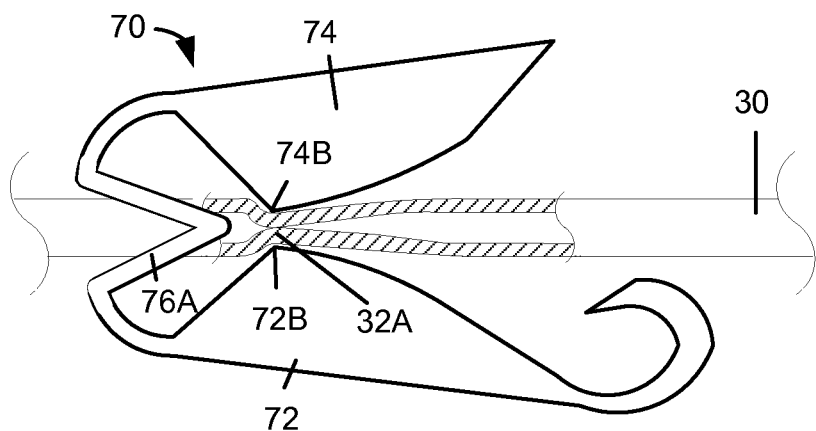
FIGS. 16 and 17 depict operational configurations of the clamp of FIG. 15 according to certain aspects of the disclosure.
Figure 17:
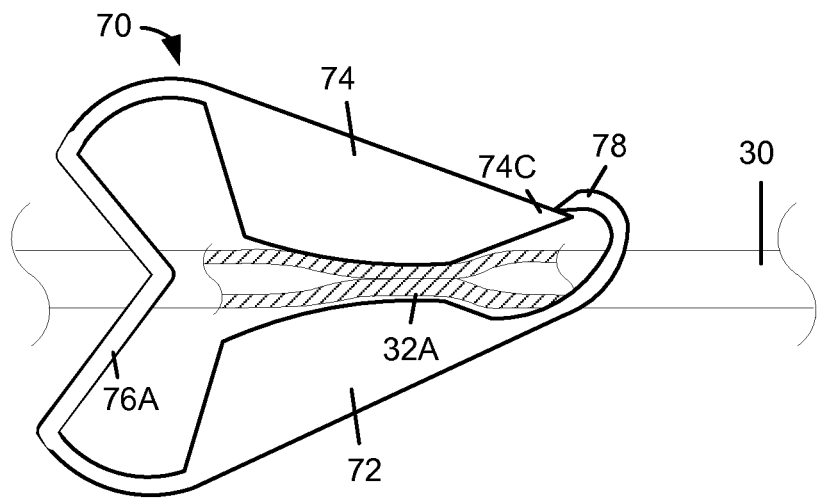

FIGS. 16 and 17 depict operational configurations of the clamp 70 of FIG. 15 according to certain aspects of the disclosure. FIG. 16 depicts the configuration of clamp 70 and tubing 30 after the clamp 70 has been partially actuated. The first element 72 has been displaced toward the second element 74 with the tubing 30 disposed between the first and second elements 72, 74. In this configuration, the first and second corners 72B, 74B have closed the gap of FIG. 15 thereby cooperatively compressing the first length 32A of the tubing 30 so as to occlude the flow channel 30A.

FIG. 17 depicts the configuration of clamp 70 and tubing 30 after the clamp 70 is fully actuated. To reach the configuration of FIG. 17 from the configuration of FIG. 16, the first element 72 is further displaced toward the second element 74. In this embodiment the first and second elements 72, 74 rotate with respect to each other along a moving contact point between the respective surfaces 72A and 72B. As the first and second elements 72, 74 rotate, the tip 74 approaches the latching tip 78 and the point of contact between surfaces 72A and 74A moves to the right, in the view of FIG. 17, from the location of first length 32A of FIG. 16 toward the location of first length 32A of FIG. 17, thereby causing the positive bolus of fluid motion out of the tubing 30 and, if this portion of tube 30 leads to the patient, the positive bolus is toward the patient. The folded section 76A of flexible element 76 has expanded to allow the rotation of the first and second elements 72, 74 with respect to each other. It can be seen that the flow channel 30A at the location of first length 32A in FIG. 16 has opened in the same location in FIG. 17. The sealingly compressed first length 32A reaches the point shown in FIG. 17 as the latching tip 78 engages the tip 74C, thereby retaining the clamp 70 in the configuration of FIG. 17.

The concepts disclosed herein provide a system and method for clamping a section of tubing, such as a line that is part of an IV set, to occlude flow through the tubing while inducing a positive bolus of fluid during the clamping process. In certain embodiments, the clamp is actuated in a manner similar to that of the prior art slide clamp.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects.

Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A clamp for clamping flexible tubing, comprising:
a body having (i) a first portion, comprising a first passage through the first portion, and (ii) a second portion comprising a second passage through the second portion, the second passage having a variable depth that increases as the second passage extends away from the first portion, wherein the first passage and the second passage defining a single slot through the body;
wherein (i) a length of the flexible tubing is compressed along a longitudinal axis from a first point to a second point when the flexible tubing is displaced perpendicular to the longitudinal axis through the first passage, and (ii) the compressed length of flexible tubing is further extended from the second point to a third point when the flexible tubing is further displaced perpendicular to the longitudinal axis from the first passage into the second passage such that the flexible tubing is compressed from the first point to the third point.

2. The clamp of claim 1, wherein:
the first and second passages are parts of a continuous slot through the body;
the first portion of the body has a first thickness at the first passage; and
the second portion of the body has a second thickness at the second passage, the second thickness being greater than the first thickness,
whereby wherein the flexible tubing is laterally displaceable between the first passage and second passage.

3. The clamp of claim 2, wherein:
the first and second portions of the body share a common planar surface;
the continuous slot passes through the common planar surface;
the first portion of the body is substantially uniform in thickness; and
the second portion of the body varies in thickness.

4. The clamp of claim 1, further comprising a non-obstructing passage through the first portion, the non-obstructing passage contiguous with the first passage, the non-obstructing passage configured such that the flexible tube is not compressed when the flexible tube is disposed to pass through the non-obstructing passage.

5. The clamp of claim 4, wherein the body is configured to completely enclose the first passage and the second passage such that the flexible tube passing through the first passage or the second passage cannot be laterally displaced so as to become separated from the clamp.

* * * * *